(12) United States Patent
Amayev

(10) Patent No.: US 9,433,536 B1
(45) Date of Patent: Sep. 6, 2016

(54) OINTMENT-CONTAINING FOOT WRAP

(71) Applicant: Rami Amayev, Maple (CA)

(72) Inventor: Rami Amayev, Maple (CA)

(*) Notice: Subject to any disclaimer, the term of this patent is extended or adjusted under 35 U.S.C. 154(b) by 11 days.

(21) Appl. No.: 14/615,744

(22) Filed: Feb. 6, 2015

(51) Int. Cl.
| | |
|---|---|
| A61F 13/06 | (2006.01) |
| A61L 15/44 | (2006.01) |
| A61L 15/58 | (2006.01) |
| A61L 15/52 | (2006.01) |
| A43B 7/00 | (2006.01) |
| A61F 13/00 | (2006.01) |
| A61M 35/00 | (2006.01) |

(52) U.S. Cl.
CPC .............. *A61F 13/064* (2013.01); *A43B 7/00* (2013.01); *A61F 13/067* (2013.01); *A61L 15/44* (2013.01); *A61L 15/52* (2013.01); *A61L 15/58* (2013.01); *A61F 2013/00902* (2013.01); *A61F 2013/00906* (2013.01); *A61L 2300/204* (2013.01); *A61L 2300/22* (2013.01); *A61M 35/00* (2013.01)

(58) Field of Classification Search
CPC .................. A61H 35/006; A61F 2013/00485; A61F 2013/00574; A61F 13/06; A61F 13/064; A61F 13/067; A61F 13/069; A43B 3/106

USPC ............................................ 604/293; 36/50.1
See application file for complete search history.

(56) References Cited

U.S. PATENT DOCUMENTS

| | | | |
|---|---|---|---|
| 2,664,087 A | 12/1953 | Lewis | |
| 3,882,868 A * | 5/1975 | Tundermann | A61F 13/068 604/293 |
| 4,341,208 A * | 7/1982 | Gordon | A61B 10/0035 424/449 |
| 6,684,411 B1 | 2/2004 | Bachert et al. | |
| 6,874,253 B2 | 4/2005 | Hollis-Lorent | |

* cited by examiner

*Primary Examiner* — Peter S Vasat
(74) *Attorney, Agent, or Firm* — Crossley and Stevenson Intellectual Property Law

(57) ABSTRACT

An ointment-containing foot wrap including a base having a top layer and a flexible, waterproof bottom layer, an inner side, an outer side, a front side and a rear side. A center section is longitudinally disposed between the front and rear side. A pouch with an external side and an open internal side is disposed along each of the base outer side, and a portion of the front side. An ointment is continuously disposed within the center section. A cover is continuously removably disposed atop the center section. An adhesive strip is disposed along an outer perimeter of the inner side, a portion of the front side adjacent the pouch, a portion of the rear side, and an inner perimeter of the pouch. A removable backing is continuously disposed atop the adhesive strip.

4 Claims, 3 Drawing Sheets

OINTMENT-CONTAINING FOOT WRAP

CROSS-REFERENCE TO RELATED APPLICATIONS

Not Applicable

FEDERALLY SPONSORED RESEARCH OR DEVELOPMENT

Not Applicable

INCORPORATION BY REFERENCE OF MATERIAL SUBMITTED ON A COMPACT DISK

Not Applicable

BACKGROUND OF THE INVENTION

Various types of footwear are known in the prior art. However, what is needed is an ointment-containing foot wrap. Many people struggle with calluses and dry, cracked skin on their heels and soles of their feet. The present device helps to heal said calluses and dry, cracked skin. The present device conforms to the users foot and the foot is secured within the ointment-containing foot wrap by an adhesive strip. The conformity of the ointment-containing foot wrap allows an ointment to properly penetrate the skin on the heel and sole of the feet. The ointment-containing foot wrap allows the user to wear the device inside of socks, shoes, boots, and other footwear for up to three days. The ointment-containing foot wrap is easily removed and disposed of after use. The ointment-containing foot wrap fulfills the need for a means of providing the user with a quick and simple way to soften calluses and dry skin of the feet. The ointment-containing foot wrap is convenient, cost-effective, durable and light weight. The ointment-containing foot wrap moistens and softens the skin on the feet for comfortable, smooth and healthy feet. The ointment-containing foot wrap completely seals in the foot, enhancing the effect of the ointment. The ointment-containing wrap eliminates the use of traditional, difficult to handle and time consuming methods to remove layers of dead skin and hardened calluses from the feet. A base of the device has a bottom layer that is waterproof and impermeable, preventing the passage of the ointment while the ointment-containing foot wrap is sealed on the user's foot.

FIELD OF THE INVENTION

The present invention relates to footwear, and more particularly, to an ointment-containing foot wrap.

SUMMARY OF THE INVENTION

The general purpose of the present ointment-containing foot wrap, described subsequently in greater detail, is to provide a an ointment-containing foot wrap which has many novel features that result in an ointment-containing foot wrap which is not anticipated, rendered obvious, suggested, or even implied by prior art, either alone or in combination thereof.

To accomplish this, the present ointment-containing foot wrap includes a base. The base has a top layer, a flexible, waterproof bottom layer, an inner side, an outer side, a front side, a rear side, and a center section longitudinally disposed between the front side and the rear side. The center section is configured to receive a sole of a user's foot thereon.

A pouch having an external side is continuously disposed along each of the base outer side and a portion of the front side. The pouch is configured to receive an outer portion of the user's foot therein. The pouch has an open internal side. An ointment is continuously disposed within the center section.

A cover is continuously removably disposed atop the center section. The cover is configured to conceal the ointment and alternately expose the ointment upon removal of the cover.

An adhesive strip is continuously disposed along each of an outer perimeter of the inner side, a portion of the front side adjacent the pouch, a portion of the rear side, and an inner perimeter of the pouch. The adhesive strip is configured to secure a portion of the inner side to the outer side proximal the front side, and to secure a portion of each of the inner side and the outer side atop the user's foot.

A removable backing is continuously disposed atop the adhesive strip The backing prevents undesired sticking of the adhesive before use and alternately upon removal of the backing exposes the adhesive.

The inner side is configured to wrap across the user's foot and a portion of the pouch proximal the front side. The base has a size, a length, and a shape configured to substantially conform to the user's foot.

Thus has been broadly outlined the more important features of the present ointment-containing foot wrap so that the detailed description thereof that follows may be better understood and in order that the present contribution to the art may be better appreciated.

BRIEF DESCRIPTION OF THE DRAWINGS

Figures

DETAILED DESCRIPTION OF THE DRAWINGS

Figure 1:
FIG. 1 is a side elevation folded view.
Figure 2:
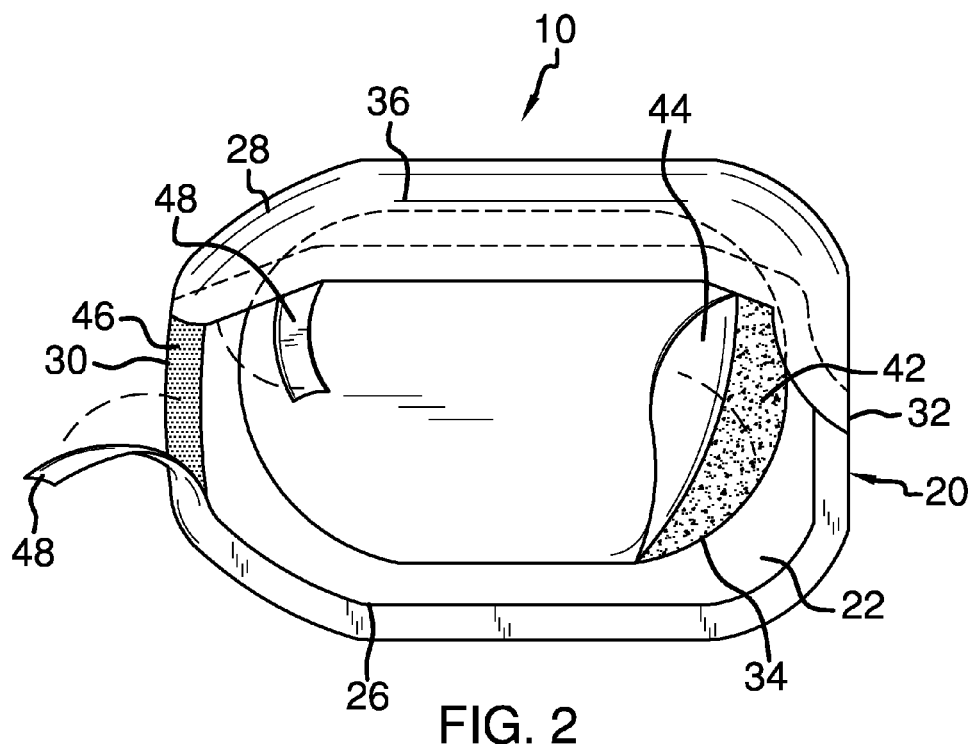
FIG. 2 is a top elevation open view.
Figure 3:
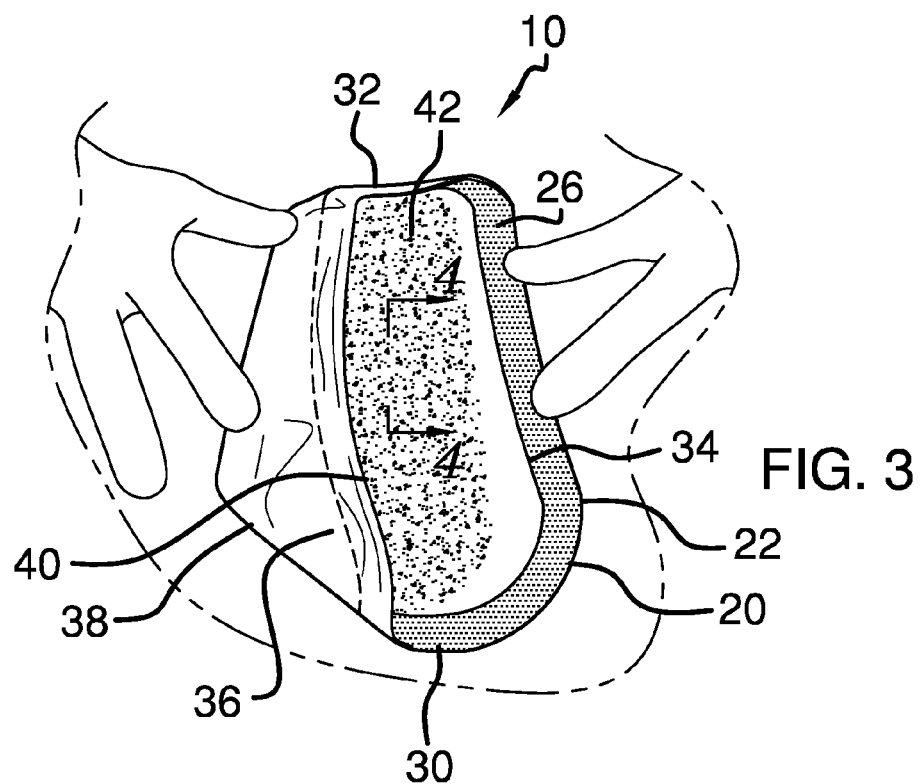
FIG. 3 is a detail view.
Figure 4:
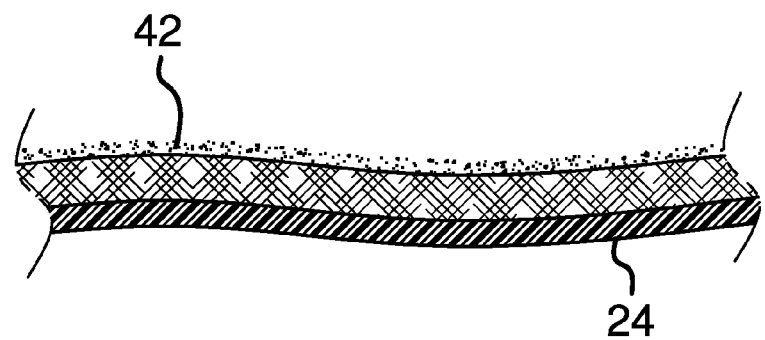
FIG. 4 is a cross-sectional view taken along line 4-4 of FIG. 3.
Figure 5:
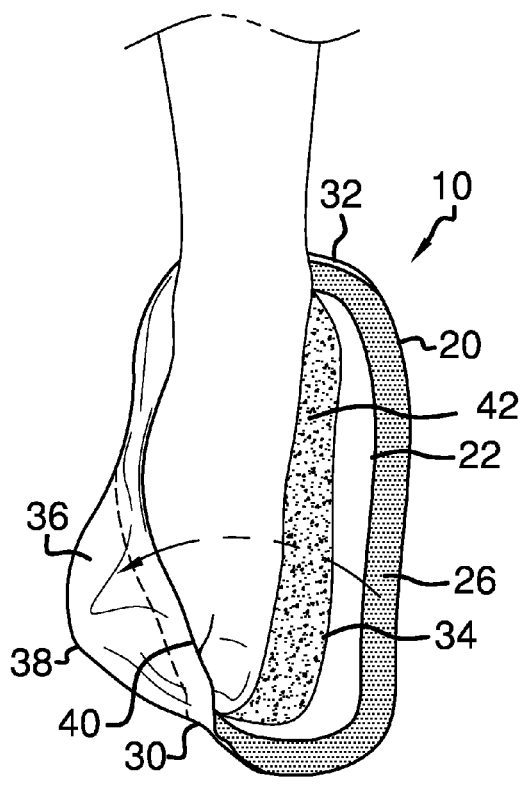
FIG. 5 is an in-use detail view.
Figure 6:
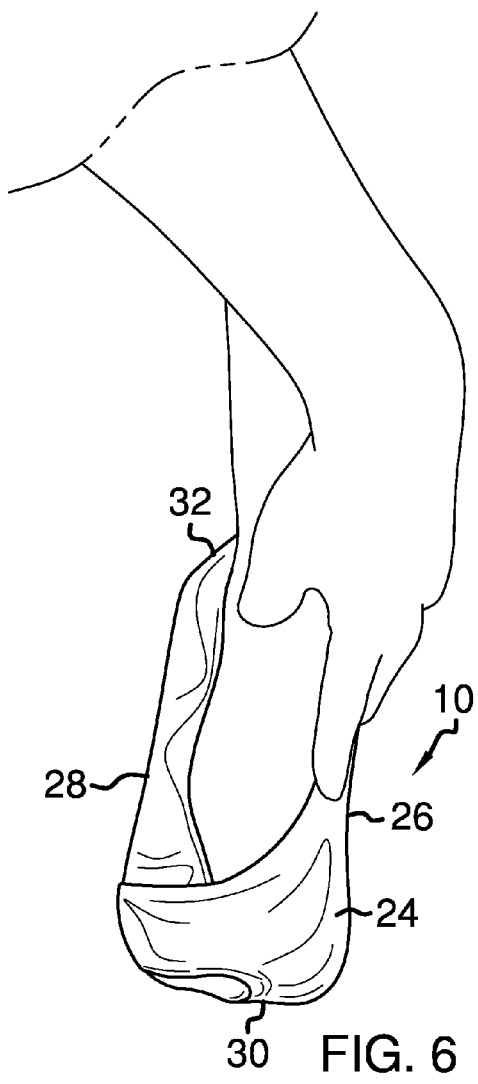
FIG. 6 is an in-use detail view

With reference now to the drawings, and in particular FIGS. 1 through 6 thereof, an example of the instant ointment-containing foot wrap employing the principles and concepts of the present ointment-containing foot wrap and generally designated by the reference number 10 will be described.

Referring to FIGS. 1 through 6 the present ointment-containing foot wrap 10 is illustrated. The ointment-containing foot wrap 10 includes a base 20. The base 20 has a top layer 22, a bottom layer 24, an inner side 26, an outer side 28, a front side 30, a rear side 32, and a center section 34 longitudinally disposed between the front side 30 and the rear side 32. The center section 34 is configured to receive a sole of a user's foot thereon.

A pouch 36 having an external side 38 is continuously disposed along each of the base 20 outer side 28 and a portion of the front side 30. The pouch 36 is configured to receive an outer portion of the user's foot therein. The pouch 36 has an open internal side 40. An ointment 42 is continuously disposed within the center section 34.

A cover 44 is continuously removably disposed atop the center section 34. The cover 44 is configured to conceal the ointment 42 and alternately expose the ointment 42 upon removal of the cover 44.

An adhesive strip 46 is continuously disposed along each of an outer perimeter of the inner side 26, a portion of the front side 30 adjacent the pouch 36, a portion of the rear side 32, and an inner perimeter of the pouch 36. The adhesive strip 46 is configured to secure a portion of the inner side 26 to the outer side 28 proximal the front side 30, and to secure a portion of each of the inner side 26 and the outer side 28 atop the user's foot.

A removable backing 48 is continuously disposed atop the adhesive strip 46. The backing 48 prevents undesired sticking of the adhesive strip 46 before use and alternately the removal of the backing 48 exposes the adhesive strip 46.

The inner side 26 is configured to wrap across the user's foot and a portion of the pouch 36 proximal the front side 30. The base 20 has a size, a length, and a shape configured to substantially conform to the user's foot.

The bottom layer 24 is flexible to allow movement of the user's foot. The bottom layer 24 is also waterproof and impermeable to prevent the passage of the ointment 42 therethrough. The ointment 42 is configured to treat and heal calluses and dry, cracked skin on the heels and soles of the user's foot. The ointment is comprised of urea, lanolin and allantoin and alternately of other desired components.

What is claimed is:

1. An ointment-containing foot wrap comprising:
   a base having a top layer, a bottom layer, an inner side, an outer side, a front side, a rear side, and a center section longitudinally disposed between the front side and the rear side, the center section being configured to receive a sole of a user's foot thereon;
   a pouch having an external side continuously disposed along each of the base outer side and a portion of the front side, the pouch configured to receive an outer portion of the user's foot therein, the pouch further having an open internal side;
   an ointment continuously disposed within an entirety of the center section;
   a cover continuously removably disposed atop the center section, the cover being configured to conceal the ointment and alternately expose the ointment upon removal of the cover;
   an adhesive strip continuously disposed along each of an outer perimeter of the inner side, a portion of the front side adjacent the pouch, a portion of the rear side, and an inner perimeter of the pouch, the adhesive strip being configured to secure a portion of the inner side to the outer side proximal the front side, and to secure a portion of each of the inner side and the outer side atop the user's foot;
   a removable backing continuously disposed atop the adhesive strip;
   wherein the inner side is configured to wrap across the user's foot and a portion of the pouch proximal the front side;
   wherein the base has a size, a length, and a shape configured to substantially conform to the user's foot.

2. The ointment-containing foot wrap of claim 1 wherein the bottom layer is waterproof.

3. The ointment-containing foot wrap of claim 1 wherein the bottom layer is flexible.

4. An ointment-containing foot wrap comprising:
   a base having a top layer, a flexible, waterproof, bottom layer, an inner side, an outer side, a front side, a rear side, and a center section longitudinally disposed between the front side and the rear side, the center section being configured to receive a sole of a user's foot thereon;
   a pouch having an external side continuously disposed along each of the base outer side and a portion of the front side, the pouch configured to receive an outer portion of the user's foot therein, the pouch further having an open internal side;
   an ointment continuously disposed within an entirety of the center section;
   a cover continuously removably disposed atop the center section, the cover being configured to conceal the ointment and alternately expose the ointment upon removal of the cover;
   an adhesive strip continuously disposed along each of an outer perimeter of the inner side, a portion of the front side adjacent the pouch, a portion of the rear side, and an inner perimeter of the pouch, the adhesive strip being configured to secure a portion of the inner side to the outer side proximal the front side, and to secure a portion of each of the inner side and the outer side atop the user's foot;
   a removable backing continuously disposed atop the adhesive strip;
   wherein the inner side is configured to wrap across the user's foot and a portion of the pouch proximal the front side;
   wherein the base has a size, a length, and a shape configured to substantially conform to the user's foot.

\* \* \* \* \*